(12) United States Patent
Heraty et al.

(10) Patent No.: US 9,314,353 B2
(45) Date of Patent: Apr. 19, 2016

(54) STENT SUITABLE FOR DEPLOYMENT IN A BLOOD VESSEL

(75) Inventors: Kevin Heraty, Castlebar (IE); Liam Mullins, Athlone (IE)

(73) Assignee: Veryan Medical Limited, Oxford (GB)

( * ) Notice: Subject to any disclaimer, the term of this patent is extended or adjusted under 35 U.S.C. 154(b) by 0 days.

(21) Appl. No.: 13/123,094

(22) PCT Filed: Oct. 12, 2009

(86) PCT No.: PCT/GB2009/002437
§ 371 (c)(1),
(2), (4) Date: Jun. 23, 2011

(87) PCT Pub. No.: WO2010/041040
PCT Pub. Date: Apr. 15, 2010

(65) Prior Publication Data
US 2011/0251671 A1    Oct. 13, 2011

Related U.S. Application Data

(63) Continuation-in-part of application No. 12/249,389, filed on Oct. 10, 2008, now Pat. No. 9,149,377.

(30) Foreign Application Priority Data

Oct. 10, 2008   (EP) ..................................... 08253318

(51) Int. Cl.
| | | |
|---|---|---|
| A61F 2/89 | (2013.01) | |
| A61F 2/915 | (2013.01) | |
| A61F 2/91 | (2013.01) | |
| A61F 2/82 | (2013.01) | |

(52) U.S. Cl.
CPC . *A61F 2/915* (2013.01); *A61F 2/89* (2013.01); *A61F 2/91* (2013.01); *A61F 2002/826* (2013.01); *A61F 2250/0018* (2013.01); *A61F 2250/0036* (2013.01); *A61F 2250/0039* (2013.01)

(58) Field of Classification Search
CPC ................ A61F 2/86–2/94; A61F 2230/0063; A61F 2203/0091
USPC ........................................................ 623/1.22
See application file for complete search history.

(56) References Cited

U.S. PATENT DOCUMENTS

| | | | | |
|---|---|---|---|---|
| 4,531,933 A | * | 7/1985 | Norton et al. ...................... 604/8 |
| 4,681,570 A | * | 7/1987 | Dalton .......................... 604/524 |

(Continued)

FOREIGN PATENT DOCUMENTS

| | | | | |
|---|---|---|---|---|
| EP | 0 800 801 A1 | 10/1997 | | |
| EP | 1279382 A1 | * | 1/2003 | ................ A61F 2/06 |

(Continued)

OTHER PUBLICATIONS

Abstract of patent WO 0069366A1 of Lefebvre.*

(Continued)

*Primary Examiner* — Paul Prebilic
(74) *Attorney, Agent, or Firm* — Fay Sharpe LLP

(57) ABSTRACT

A stent suitable for deployment in a blood vessel to support at least part of an internal wall of the blood vessel includes a central section, a first intermediate section, a first end section, a second intermediate section and a section end section. The stent is movable between a delivery configuration and a deployment configuration.

12 Claims, 9 Drawing Sheets

(56) References Cited

U.S. PATENT DOCUMENTS

| | | | |
|---|---|---|---|
| 4,813,925 A * | 3/1989 | Anderson et al. | 604/8 |
| 5,749,919 A * | 5/1998 | Blanc | 623/1.22 |
| 5,938,697 A * | 8/1999 | Killion et al. | 623/1.15 |
| 5,984,965 A * | 11/1999 | Knapp et al. | 623/23.7 |
| 6,027,526 A * | 2/2000 | Limon et al. | 623/1.15 |
| 6,673,102 B1 | 1/2004 | Vonesh et al. | |
| 6,685,738 B2 | 2/2004 | Chouinard et al. | |
| 7,326,240 B1 * | 2/2008 | Caro et al. | 623/1.15 |
| 9,149,377 B2 * | 10/2015 | Heraty | A61F 2/91 |
| 2001/0031981 A1 * | 10/2001 | Evans et al. | 606/200 |
| 2001/0049549 A1 * | 12/2001 | Boylan et al. | 623/1.11 |
| 2002/0095206 A1 * | 7/2002 | Addonizio et al. | 623/1.15 |
| 2003/0135265 A1 * | 7/2003 | Stinson | 623/1.16 |
| 2003/0208256 A1 * | 11/2003 | DiMatteo et al. | 623/1.11 |
| 2004/0044400 A1 * | 3/2004 | Cheng et al. | 623/1.16 |
| 2004/0087886 A1 * | 5/2004 | Gellman | 604/8 |
| 2004/0088043 A1 | 5/2004 | Klein | |
| 2004/0133266 A1 * | 7/2004 | Clerc et al. | 623/1.22 |
| 2004/0193254 A1 * | 9/2004 | Greenberg et al. | 623/1.35 |
| 2004/0243216 A1 | 12/2004 | Gregorich | |
| 2006/0015173 A1 * | 1/2006 | Clifford et al. | 623/1.16 |
| 2006/0184232 A1 | 8/2006 | Gianotti et al. | |
| 2006/0229695 A1 | 10/2006 | Brown et al. | |
| 2006/0247759 A1 | 11/2006 | Burpee et al. | |
| 2006/0265051 A1 | 11/2006 | Caro et al. | |
| 2007/0129786 A1 * | 6/2007 | Beach et al. | 623/1.15 |
| 2007/0156078 A1 * | 7/2007 | Caro et al. | 604/8 |
| 2007/0185563 A1 | 8/2007 | Zarbatany et al. | |
| 2007/0191927 A1 * | 8/2007 | Bowe et al. | 623/1.15 |
| 2007/0293932 A1 * | 12/2007 | Zilla et al. | 623/1.11 |
| 2008/0262599 A1 * | 10/2008 | Caro et al. | 623/1.16 |
| 2012/0016460 A1 * | 1/2012 | Heraty et al. | 623/1.15 |

FOREIGN PATENT DOCUMENTS

| | | | |
|---|---|---|---|
| GB | 2 418 362 A | 3/2006 | |
| JP | 2006-520630 | 9/2006 | |
| JP | 2008-513171 | 5/2008 | |
| JP | 2008-535627 A | 9/2008 | |
| WO | WO 98/22159 | 5/1998 | |
| WO | WO 00/28922 | 5/2000 | |
| WO | WO 00/32241 | 6/2000 | |
| WO | WO 0069366 A1 * | 11/2000 | A61F 2/06 |
| WO | WO 03/057079 A1 | 7/2003 | |
| WO | WO 2004/082533 | 9/2004 | |
| WO | WO 2004/082533 A1 | 9/2004 | |
| WO | WO 2004082520 A2 * | 9/2004 | |
| WO | WO 2006/032902 | 3/2006 | |
| WO | WO 2007/131798 | 11/2007 | |

OTHER PUBLICATIONS

European Search Report corresponding to EP 08 25 3318, Jan. 16, 2009 (English Text).

International Search Report of International Application No. PCT/GB2009/002437 dated Feb. 15, 2010 (English Text).

Written Opinion of the International Searching Authority of International Application No. PCT/GB2009/002437 dated Feb. 15, 2010 (English Text).

\* cited by examiner

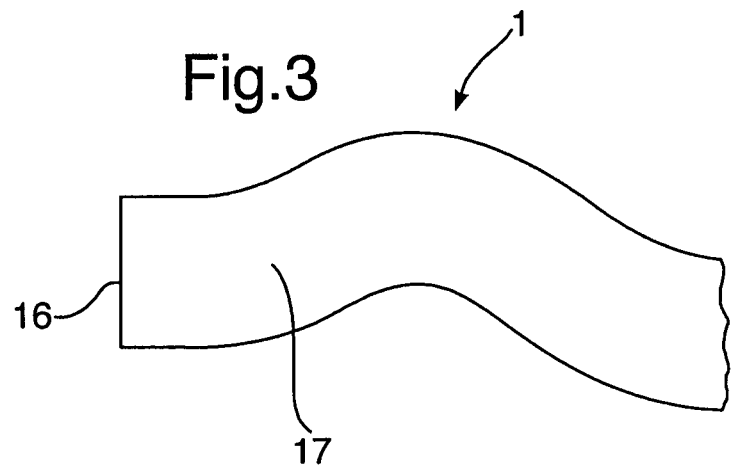
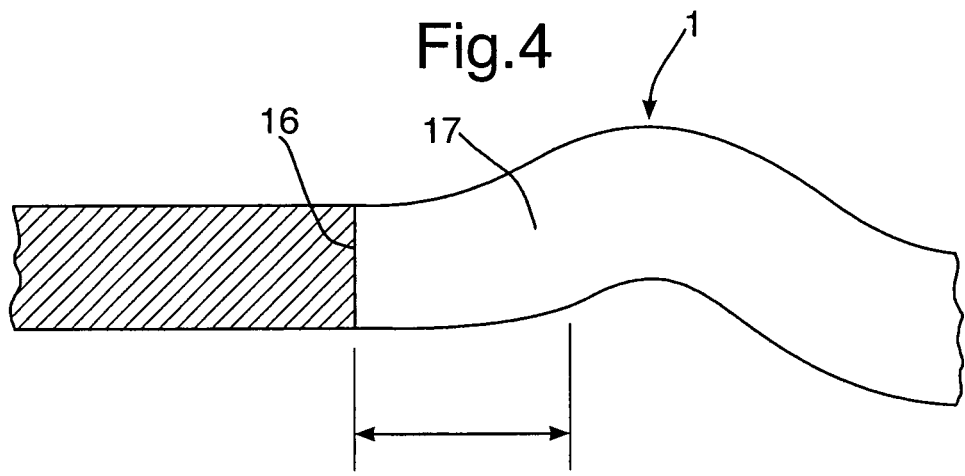

STENT SUITABLE FOR DEPLOYMENT IN A BLOOD VESSEL

This application is a continuation-in-part of U.S. application Ser. No. 12/249,389 which was filed on Oct. 10, 2008 now U.S. Pat. No. 9,149,377.

INTRODUCTION

This invention relates to a stent suitable for deployment in a blood vessel to support at least part of an internal wall of the blood vessel.

STATEMENTS OF INVENTION

According to the invention there is provided a stent suitable for deployment in a blood vessel to support at least part of an internal wall of the blood vessel, the stent being movable between a delivery configuration and a deployment configuration.

In one embodiment of the invention the stent comprises a first region and a second region, the radial stiffness of the first region being greater than the radial stiffness of the second region. This arrangement reduces the area of the internal wall of the blood vessel which has low wall shear stress, reduces the possibility of recirculation, and reduces the risk of neointimal hyperplasia. Wall shear stress is generated on the internal wall of a blood vessel by flow adjacent to the wall. Levels of mean wall shear stress below 0.4 Pa have been shown to have a pathogenic effect on endothelial cells which cover the inner surface of the arteries. Higher levels of wall shear stress, for example greater than 1.5 Pa, have been associated with a reduction in levels of in-stent restenosis. Preferably the radial stiffness varies gradually from the first region towards the second region. Ideally the second region is closer to an end of the stent than the first region. Most preferably the second region is located at an end of the stent.

In one case the stent comprises a plurality of annular elements or crowns. Preferably the longitudinal dimension of an annular element in the first region is less than the longitudinal dimension of an annular element in the second region. In this manner the radial stiffness is reduced by increasing the longitudinal dimension of the annular element. Ideally the longitudinal dimension of the annular element in the second region is between 1% and 90% greater than the longitudinal dimension of the annular element in the first region. Most preferably the longitudinal dimension of the annular element in the second region is between 1% and 75% greater than the longitudinal dimension of the annular element in the first region. The longitudinal dimension of the annular element in the second region may be approximately 40% greater than the longitudinal dimension of the annular element in the first region.

The thickness of the annular element in the first region may be greater than the thickness of the annular element in the second region. In this manner the radial stiffness is reduced by reducing the thickness of the annular element. In this specification, the term 'thickness' will be understood to mean the dimension in the radial direction.

The stent may comprise one or more connecting elements to connect a first annular element to a second annular element. Preferably the connecting element extends from the first annular element to the second annular element in a non-straight configuration. Ideally the connecting element extends from the first annular element to the second annular element in a substantially curved configuration.

The stent may comprise interconnected strut elements.

The annular element may comprise a plurality of interconnected strut elements.

Preferably the length of the strut element in the first region is less than the length of the strut element in the second region. In this manner the radial stiffness is reduced by increasing the length of the strut element. Ideally the length of the strut element in the second region is between 1% and 90% greater than the length of the strut element in the first region. Most preferably the length of the strut element in the second region is between 1% and 75% greater than the length of the strut element in the first region. The length of the strut element in the second region may be approximately 40% greater than the length of the strut element in the first region.

The width of the strut element in the first region may be greater than the width of the strut element in the second region. In this manner the radial stiffness is reduced by reducing the width of the strut element. Preferably the width of the strut element in the first region is between 2% and 50% greater than the width of the strut element in the second region. Ideally the width of the strut element in the first region is between 10% and 30% greater than the width of the strut element in the second region. The width of the strut element in the first region is approximately 20% greater than the width of the strut element in the second region.

The thickness of the strut element in the first region may be greater than the thickness of the strut element in the second region. In this manner the radial stiffness is reduced by reducing the thickness of the strut element.

In one embodiment a first strut element is connected to a second strut element at a connection point. Preferably the connecting element is connected to the annular element at the connection point.

The thickness of the stent wall may be greater in the first region than in the second region. For example, where the stent comprises annular elements, an annular element in the first region may have a greater thickness than an annular element in the second region. Where the annular elements comprise interconnected strut elements, the strut elements in the first region may have a greater thickness than an annular element in the second region.

Where an annular element is formed by interconnected strut elements, the interconnected strut elements may have a zig-zag or sinusoidal configuration. Thus a first strut element may extend longitudinally from left, to right as it also extends in the circumferential direction, whilst an adjacent second strut element may extend from right to left as it also extends in the same circumferential direction. There may be a defined connection point between adjacent strut elements, e.g. in a zig-zag configuration, or a smoother transition between the two, e.g. in a sinusoidal configuration.

Preferably the stent is non-woven.

In certain embodiments, when the stent is in use, in the deployment configuration and in a blood vessel, the diameter of the stent reduces towards an end of the stent. By constructing the stent so that the diameter reduces towards an end of the stent in use, good apposition of the stent to the vessel wall may be maintained. This may help to regulate wall shear stress at the end of the stent which would otherwise occur due to a sudden change in the cross sectional area. In conventional stents, there may be a step change in the cross sectional area, i.e. a sudden increase, from an unstented part of the vessel to the stented part. This may result in recirculation of the blood flow and regions of low wall shear stress. If however, according to preferred embodiments, the diameter of the stent reduces towards an end of the stent when it is deployed in a vessel, then these disadvantages can be mitigated, i.e. the tendency for recirculation can be reduced and regions of low wall shear stress can be minimised.

The diameter of the stent, when in the deployment configuration and in a blood vessel, preferably tapers towards the end of the stent. By providing the end region of the stent with a taper, the transition between the diameter of the unstented part of the vessel and a wider diameter in the stented part of the vessel can be made gradual.

The reducing stent diameter towards an end thereof (e.g. a gradual tapering diameter) may occur at one end of the stent, for example to manage the transition between the unstented part of the vessel and the stented part at an inlet end or an outlet end of the stent. A reducing stent diameter at the inlet helps to manage the flow as it enters the stented part of the vessel, and is expected to be beneficial in reducing levels of in-stent restenosis. A reducing stent diameter at the outlet helps to manage the flow as it leaves the stented part of the vessel and in particular may be beneficial in reducing recirculation of the flow in the stented part, as well as improving the transition of the flow into the vessel downstream of the stent.

Preferably, the stent diameter reduction is provided at both ends of the stent. With this arrangement it may be possible to deploy the stent in a vessel without having to consider which end will be the inlet and which end the outlet.

The stent may have a section adjacent to the reducing diameter end section, for example a central section, which has a substantially constant diameter over the length of the section.

The reduction in stent diameter towards an end thereof may be achieved in various ways. One way is to vary the radial stiffness of the stent as discussed above. By reducing the radial stiffness of the stent towards an end thereof, when the stent is in the deployment configuration and is in a blood vessel, the reduced radial stiffness can cause the diameter of the stent to reduce towards an end thereof.

The reduced radial stiffness may be achieved in the case of a stent made up of annular elements by providing that the longitudinal dimension of an annular element at an end of the stent is less than the longitudinal dimension of an annular element further from the end. In certain preferred embodiments, the stent comprises a first region and a second region, the radial stiffness of the first region being greater than the radial stiffness of the second region and the second region being closer to an end of the stent than the first region, the stent comprising a plurality of annular elements, and the longitudinal dimension of an annular element in the first region being less than the longitudinal dimension of an annular element in the second region.

The reduced radial stiffness of the stent may be achieved by varying the stent wall thickness. The stent wall thickness may for example reduce towards an end of the stent. If the stent comprises strut elements, the reduced radial stiffness may be achieved by providing strut elements of reduced width.

In the preferred embodiments in which the stent diameter reduces towards an end of the stent when the stent is in the deployed configuration and is in a blood vessel, the reduction in diameter may be provided by constructing the stent so that when it is in the deployment configuration and not constrained in a blood vessel, the stent diameter reduces towards the end of the stent. Thus the actual stent diameter, when not installed in a vessel, may reduce towards the end of the stent. The variation in diameter may be achieved by forming the stent with a tooling which has the same distribution of diameter as is desired on the finished stent. If the stent has a curvature (for example with the longitudinal axis of at least at least a section curved in three-dimensional space), the tooling may have the desired curvature as well as distribution of diameter.

A combination of variation in radial stiffness and variation in stent diameter could also be used to achieve the desired effect that the diameter of the stent reduces towards an end of the stent when it is in the employment configuration and in a vessel. For example, a stent with a reduced diameter portion and also reduced radial stiffness could be used. The reduced radial stiffness could be due to a longer longitudinal dimension of an end annular element, or a reduced stent wall thickness (e.g. decreased strut thickness). This combination would achieve a greater tapering effect than by just varying the radial stiffness, or by just varying the diameter of the stent when not constrained in a vessel.

It is generally desirable that the tapering effect at an end of the stent should be gradual. Thus, blood may flow along an unstented part of the vessel of a given diameter, and then as it flows into the stented part at an inlet end of the stent the diameter will preferably increase gradually. At the outlet end, a taper will ensure that the vessel diameter decreases gradually towards the unstented vessel at the outlet end. If the stent comprises a plurality of annular elements, it is preferred that at least three of such elements in a longitudinal row have different properties to provide a taper. If there are only two annular elements with different properties then the change in diameter may not be as gradual as is preferred. The different properties of the annular element may be different radial stiffnesses or different diameters (when the stent is not constrained in a vessel), or a combination of the two.

In one case in the deployment configuration the longitudinal axis of at least a section of the stent is curved in three-dimensional space. When the stent is deployed in the blood vessel, the stent exerts force on the blood vessel causing at least part of the longitudinal axis of the blood vessel to curve in three-dimensional space. Blood flowing through the three-dimensional curved part of the blood vessel then undergoes a swirling action. The swirling flow of blood has been found to minimise thrombosis and platelet adhesion, and to minimise or prevent coverage of the stent by ingrowth of intima. The flow pattern in the blood vessel including the swirling pattern induced by the non-planar geometry of the blood vessel operates to inhibit the development of vascular diseases such as thrombosis/atherosclerosis and intimal hyperplasia. In the deployment configuration the three-dimensional curved section may be substantially helically shaped. In the deployment configuration the three-dimensional curved section may be substantially spiral shaped. In the delivery configuration the longitudinal axis of the three-dimensional curved section may be substantially straight. Ideally in the delivery configuration the three-dimensional curved section is substantially cylindrically shaped. The cylindrical shape provides a low-profile for ease of delivery.

In the deployment configuration the longitudinal axis of at least a section of the stent may be substantially straight. Most preferably in the deployment configuration the straight section is substantially cylindrically shaped.

At least a section of the stent may have a helical angle which varies along the length of the section. This arrangement reduces the area of the internal wall of the blood vessel which has low wall shear stress, reduces the possibility of recirculation, and reduces the risk of neointimal hyperplasia. Preferably the helical angle varies gradually along the length of the varying helical angle section. The helical angle at one end of the varying helical angle section may be in the range of from 5° to 60°. Preferably the helical angle at one end of the varying helical angle section is in the range of from 15° to 45°.

Ideally the helical angle at one end of the varying helical angle section is approximately 30°. The helical angle at the other end of the varying helical angle section may be approximately 0°. The helical angles discussed herein are those when the stent is in its deployment configuration but not constrained by being in a vessel. When the stent is in a vessel there may be a tendency for it to be straightened out and hence a reduction in the helix angle.

The stent may comprise a first end section and a second end section. Preferably the longitudinal axis of the first end section is substantially parallel to the longitudinal axis of the second end section. Ideally the longitudinal axis of the first end section is substantially co-linear with the longitudinal axis of the second end section.

The invention provides in one case a stent having varying radial stiffness. The radial stiffness may be less at one end or both ends. The stiffness may be reduced by reducing the stent wall thickness, for example the strut thickness. The radial stiffness may be tapered towards the end of the stent. In this manner arterial injury at the stent ends may be reduced or avoided. The invention may also help to regulate wall shear stress at the inlet and outlet which may occur due to a sudden change in cross sectional area.

BRIEF DESCRIPTION OF THE DRAWINGS

The invention will be more clearly understood from the following description of some embodiments thereof, given by way of example only, with reference to the accompanying drawings, in which:

FIG. 3 is a side view of part of the stent of FIG. 1 in the deployment configuration before deployment in a blood vessel, FIG. 4 is a side view of the part of the stent of FIG. 3 in the deployment configuration after deployment in a blood vessel.

DETAILED DESCRIPTION

Figure 1:
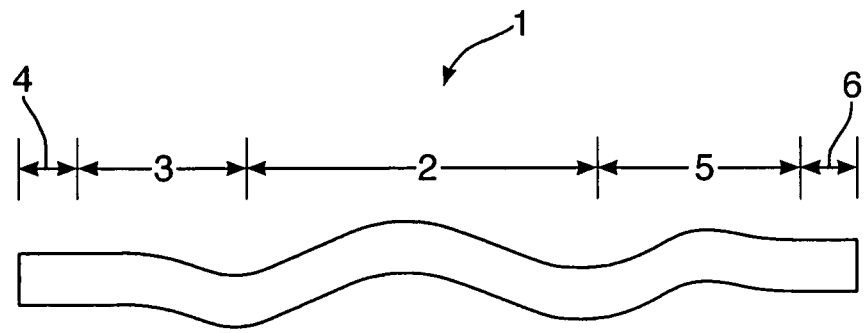
FIG. 1 is a side view of a stent according to the invention in a deployment configuration.

Referring to the drawings, and initially to FIG. 1 thereof, there is illustrated a stent 1 according to the invention. The stent 1 is suitable for deployment in a blood vessel to support at least part of an internal wall of the blood vessel.

The stent 1 comprises a central section 2, a first intermediate section 3, a first end section 4, a second intermediate section 5, and a second end section 6. The first intermediate section 3 connects the central section 2 and the first end section 4. Similarly the second intermediate section 5 connects the central section 2 and the second end section 6.

The stent 1 is movable between a collapsed delivery configuration and an expanded deployment configuration (FIG. 1). In the delivery configuration the longitudinal axis of the central section 2 is substantially straight. In particular in the delivery configuration the central section 2, the first intermediate section 3, the first end section 4, the second intermediate section 5, and the second end section 6 are all cylindrically shaped. In the deployment configuration the longitudinal axis of the central section 2 is curved in three-dimensional space. In the deployment configuration the longitudinal axis of the first end section 4 and the longitudinal axis of the second end section 6 are both substantially straight. In particular in the deployment configuration the central section 2 is helically shaped, while the first end section 4 and the second end section 6 remain cylindrically shaped (FIG. 1).

In this case the stent 1 is of a shape memory material such as Nitinol. It will be appreciated that the stent 1 may alternatively be of other materials, such as 316 L stainless steel.

In the delivery configuration and in the deployment configuration, the longitudinal axis of the first end section 4 is parallel to and co-linear with the longitudinal axis of the second end section 6, as illustrated in FIG. 1.

FIG. 1 illustrates the blended regions 3, 5, and the helical region 2. The stent and vessel centrelines are co-linear.

In an alternative arrangement, the longitudinal axis of the first end section may be parallel to and offset from the longitudinal axis of the second end section.

The first intermediate section 3 has a helical angle α which varies gradually along the length of the first intermediate section 3 from the central section 2 towards the first end section 4. Similarly the second intermediate section 5 has a helical angle α which varies gradually along the length of the second intermediate section 5 from the central section 2 towards the second end section 6. Each intermediate section 3, 5 acts as a blended region to provide a smooth transition from the helical shape of the central section 2 to the cylindrical shape of the unstented blood vessel.

The helical angle α at the central section 2 may be in the range of from 5° to 60°, preferably in the range of from 15° to 45°, and in this case is approximately 30°.

Figure 2:
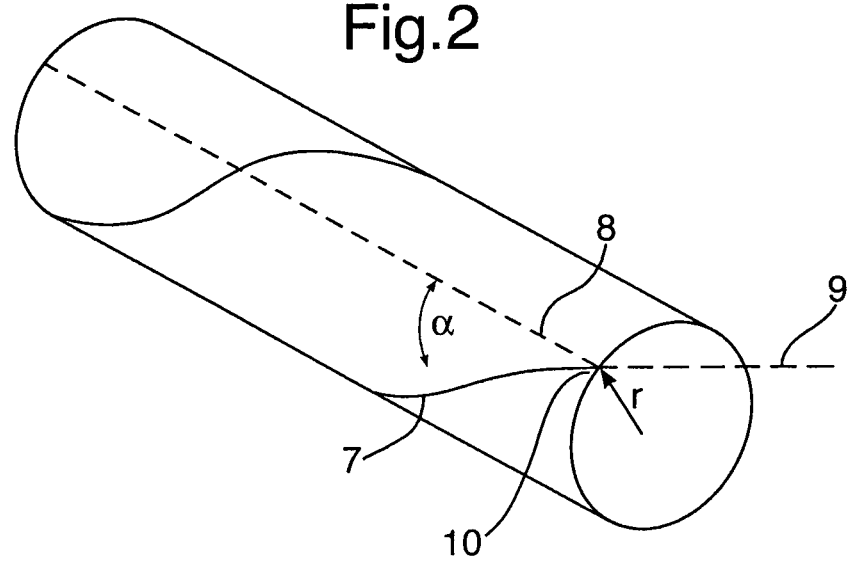
FIG. 2 is a schematic isometric view to illustrate definition of a helical angle.

The definition of the helical angle α is illustrated in FIG. 2. Consider the helical line 7 shown in FIG. 2. Every helical line may be described by the radius r of the cylinder it lies on and the helical angle α. The helical angle α is described as the angle subtended by a parallel line 8 and a tangential line 9. The parallel line 8 is a line lying on the cylinder and parallel to the centreline of the cylinder. The tangential line 9 is a line tangential to the helical line 7 at the point of intersection 10 of the parallel line 8 and the helical line 7.

In this case the helical angle α varies from approximately 30° at the central section 2 to approximately 0° at the end sections 4, 6. The length of each intermediate section 3, 5 is approximately 22 mm in this case.

The stent diameter may be in range of from 2 mm to 20 min. In this case the stent diameter is approximately 6 mm.

It will be appreciated that the intermediate sections 3, 5 may have a range of helical angles and may have a range of diameters.

The definition of the helical line 7 defines the centreline path of the final forming tool geometry and therefore has a significant effect on the stent shape. The stent forming tool has a helical section towards its centre and blended regions at the proximal and distal ends. The centreline of the forming tool has a helical and blended region.

In this case the forming tool has a constant diameter and a constant cross-section over its length.

After deployment of the stent 1, the stent 1 adjusts the geometry of the blood vessel into a helical pattern. The curvature of the intermediate sections 3, 5 is matched to that of the vessel centreline, as shown in FIG. 1.

FIG. 1 illustrates the stent 1 co-linear with the blood vessel. The blended regions 3, 5 match the rate of change of centreline curvature from the helical region 2 to the straight blood vessel.

Figure 5:
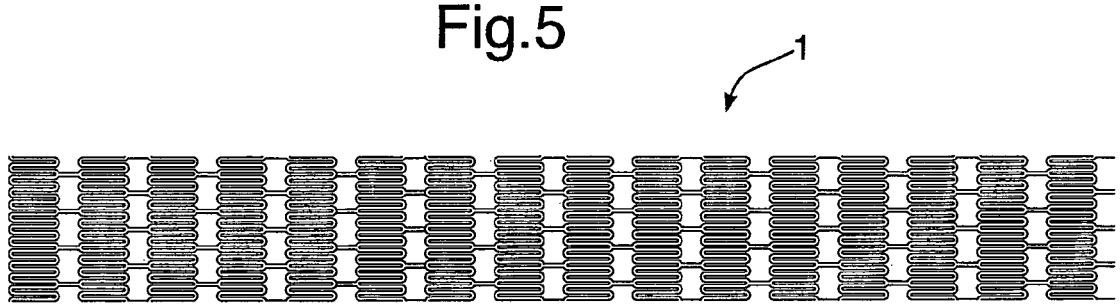
FIG. 5 is a side view of part of the stent of FIG. 1 in a delivery configuration.

FIG. 5 illustrates the stent 1 in the collapsed state.

Figure 6:
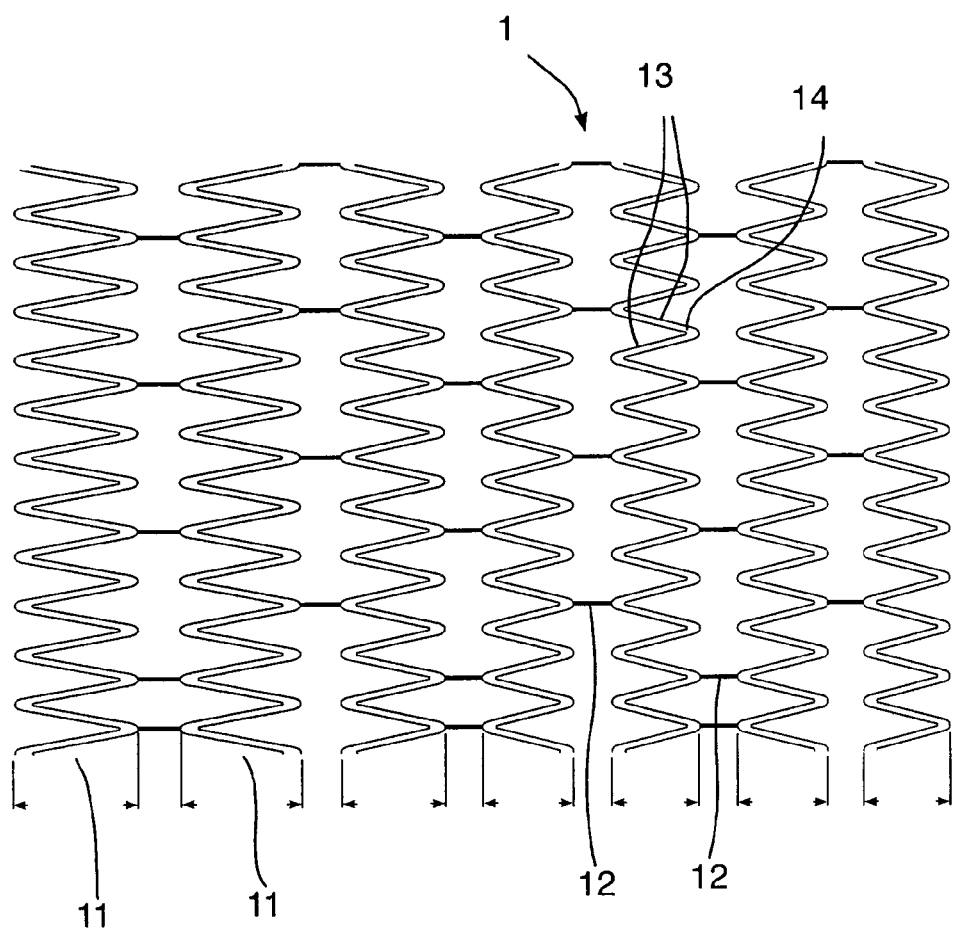
FIG. 6 is a side view of part of the stent of FIG. 1 in the deployment configuration.

As illustrated in FIG. 6, the stent 1 comprises a plurality of annular elements or crowns 11, and a plurality of connecting elements 12 to connect adjacent annular elements 11.

Each annular element 11 extends around the circumference of the stent 1. Each annular element 11 comprises a plurality of interconnected strut elements 13. Adjacent strut elements 13 are connected together at connection points 14.

Each connecting element 12 may extend from a first annular element 11 to a second annular element 11 in a straight configuration, or in a curved 'Z' shaped configuration. Each connecting element 12 is connected to the annular element 11 at a connection point 14.

It will be appreciated that the stent of the invention may have a variety of possible patterns. For example the connecting element 12 may extend from a first annular element 11 to a second annular element 11 in a curved 'S' shaped configuration. The connecting element 12 between the penultimate annular element 11 and the final annular element 11 may comprise a 'V' shaped portion.

Figure 8:
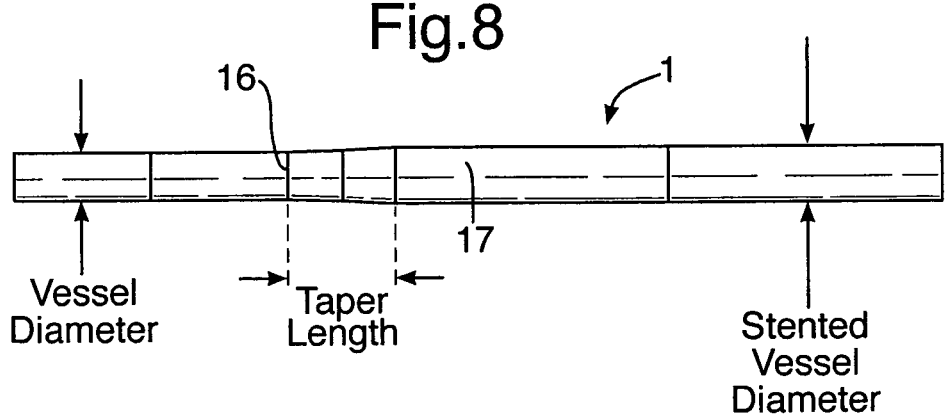
FIG. 8 is a side view of part of the stent of FIG. 1 in the deployment configuration.

The radial stiffness of the stent 1 varies gradually along part of the length of the stent 1, as illustrated in FIG. 8. In particular the radial stiffness of the end region 16 of the stent 1 is less than the radial stiffness of a first region 17 located further in from the end of the stent 1. The radial stiffness of the stent 1 varies gradually from the first region 17 towards the end region 16.

In this case the first region 17 is located approximately 8 mm from the end region 16.

The variation in radial stiffness may be achieved by a variety of different means.

For example the longitudinal dimension of the annular element 11 in the first region 17 may be less than the longitudinal dimension of the annular element 11 in the end region 16, as illustrated in FIG. 6. The longitudinal dimension of the annular element 11 in the end region 16 may be between 1% and 90% greater than the longitudinal dimension of the annular element 11 in the first region 17, preferably between 1% and 75% greater, and in this case is approximately 40% greater. Similarly the length of the strut elements 13 in the first region 17 may be less than the length of the strut elements 13 in the end region 16. The length of the strut elements 13 in the end region 16 may be between 1% and 90% greater than the length of the strut elements 13 in the first region 17, preferably between 1% and 75% greater, and in this case is approximately 40% greater.

FIG. 6 illustrates the variation in radial stiffness using strut length.

Figure 7:
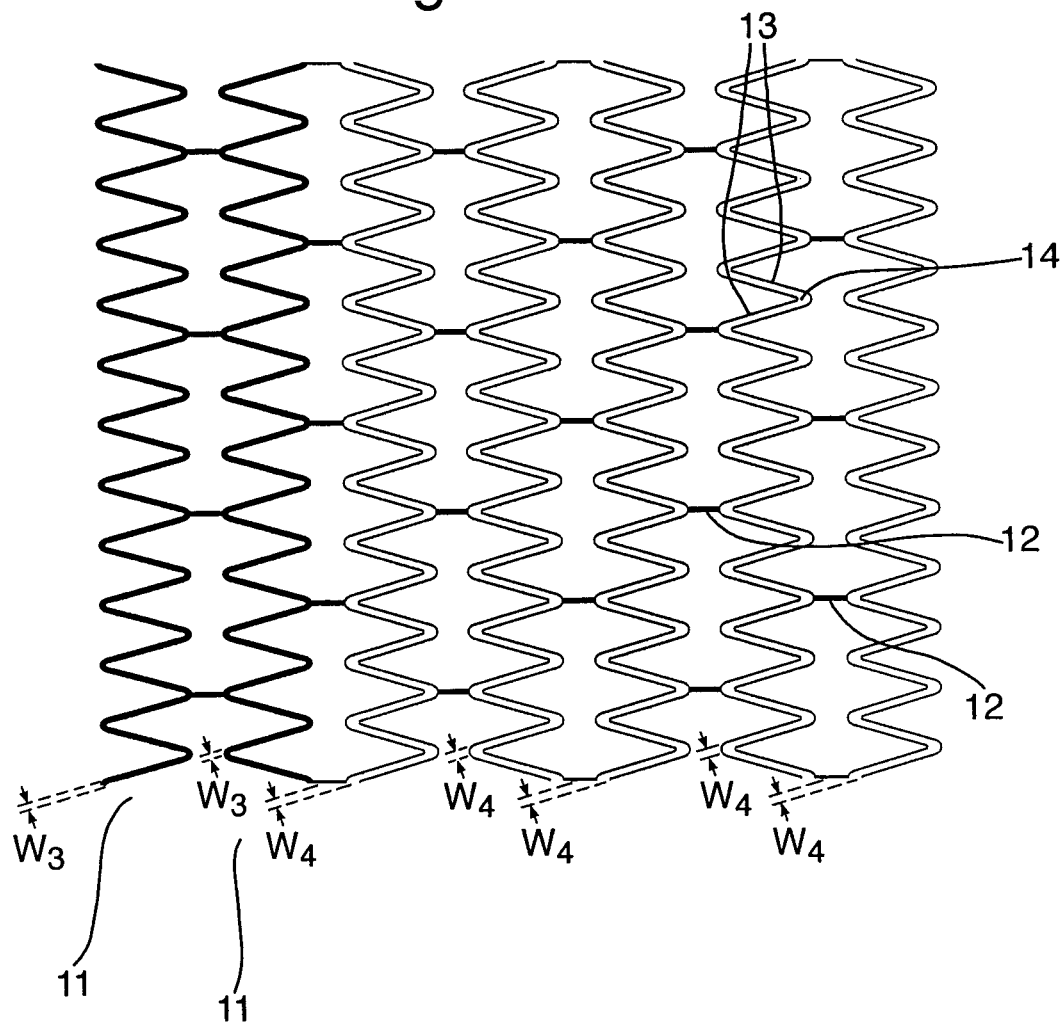
FIG. 7 is a side view of part of another stent according to the invention in the deployment configuration.

As another example the width of the strut elements 13 in the first region 17 may be greater than the width of the strut elements 13 in the end region 16, as illustrated in FIG. 7. The width of the strut elements 13 in the first region 17 may be between 2% and 50% greater than the width of the strut elements 13 in the end region 16, preferably between 10% and 30% greater, and in this case is approximately 20% greater.

FIG. 7 illustrates the variation in radial stiffness using strut width.

As another example the thickness of the annular element 11 in the first region 17 may be greater than the thickness of the annular element 11 in the end region 16. Similarly the thickness of the strut elements 13 in the first region 17 may be greater than the thickness of, the strut elements 13 in the end region 16.

Prior to delivery when the stent 1 is outside of the blood vessel, the stent 1 has a constant diameter from the first region 17 to the end region 16, as illustrated in FIG. 3. After deployment of the stent 1 in the blood vessel, the stent 1 has a tapered configuration with a gradually reducing diameter from the first region 17 to the end region 16, as illustrated in FIG. 4, due to the variation in radial stiffness.

FIG. 3 illustrates the stent 1 before deployment with no taper evident at the stent end 16. FIG. 4 illustrates the stent 1 after deployment with the taper evident at the stent end 16.

The variation in radial stiffness along part of the length of the stent 1 reduces the area of blood vessel wall which has low wall shear stress, reduces the possibility of recirculation, aria reduces the risk of neointimal hyperplasia. Levels of mean wall shear stress below 0.4 Pa have been shown to have a pathogenic effect on endothelial cells which cover the inner surface of the arteries. Higher levels of wall shear stress, for example greater than 1.5 Pa, have been associated with a reduction in levels of in-stent restenosis.

An alternative arrangement of sudden expansion from a stent to a blood vessel may lead to poor performance in terms of wall shear. The invention addresses this problem by gradually changing the diameter of the stent 1 at the ends. By varying the radial stiffness of the stent 1 the invention ensures that good apposition of the stent 1 to the vessel wall is maintained. A number of approaches are possible to achieve the diameter increase at the stent ends in a gradual manner. The strut cross section may be reduced towards the stent ends, and/or the strut length may be increased towards the stent ends.

The radial stiffness is proportional to the strut width. As the strut width increases the radial force increases. The radial stiffness is inversely proportional to the strut length. As the strut length decreases the radial force increases.

No recirculation region occurs with the stent 1 with tapering radial stiffness. A recirculation region would arise at the proximal end of a non-tapered stent with constant radial stiffness due to the sudden area change at the proximal end. Increasing the length of the tapered region reduces the surface area of wall shear stress below 0.4 Pa.

The stent 1 has the blended regions 3, 5 and is tapered. In this manner the levels of wall shear stress are significantly improved. The regions of low wall shear stress are associated with in-stent restonosis. Therefore increasing the wall shear stress reduces the levels of in-stent restonosis. The tapering is achieved by varying the radial stiffness at the proximal and distal ends of the stent 1.

The invention includes a taper on the intermediate sections 3, 5. The taper is achieved by changing the radial stiffness. The rate of expansion of the taper is constant over the overall taper length. In this case the expansion is from a 5 mm vessel to a 6 mm stented diameter.

The effect of the taper on the blended region wall shear stress is as follows.

By including the tapering section at the proximal end of the stent 1, the region of low wall shear stress below 0.4 Pa is reduced when compared with a sudden expansion into a helical stent which would result in a large region of low wall shear stress at the proximal end of the stent due to the sudden area change from the 5 mm to 6 mm blood vessel.

The surface area below 0.4 Pa may be used as a metric to evaluate the performance of a tapered stent. Increasing the length of the taper on the blended regions 3, 5 reduces the surface area of wall shear stress below 0.4 Pa.

The first four crowns 11 may have reducing strut width. The last crown 11 may have longer strut length, thus helping to achieve the desired low radial stiffness without reducing the strut width.

In use, the stent 1 is arranged in the collapsed delivery configuration with the central section 2, the first intermediate section 3, the first end section 4, the second intermediate section 5, and the second end section 6 all cylindrically shaped. When the stent 1 is outside of the blood vessel, the stent 1 has a constant diameter from the first region 17 to the end region 16, as illustrated in FIG. 3. The stent 1 is delivered through a blood vessel to the desired site of treatment. The stent 1 is then moved from the delivery configuration to the expanded deployment configuration to support at least part of an internal wall of the blood vessel. In the deployment configuration the central section 2 is helically shaped, and the first end section 4 and the second end section 6 are cylindrically shaped. After deployment of the stent 1 in the blood vessel, the stent 1 has a tapered configuration with a gradually reducing diameter from the first region 17 to the end region 16, as illustrated in FIG. 4, due to the variation in radial stiffness.

When the stent 1 is deployed in the blood vessel, the stent 1 exerts force on the blood vessel causing at least part of the longitudinal axis of the blood vessel to curve in three-dimensional space. In this manner the stent 1 acts to support at least part of the internal wall of the blood vessel curved in three-dimensional space. Blood flowing through the three-dimensional curved part of the blood vessel then undergoes a swirling action. The swirling flow of blood has been found to minimise thrombosis and platelet adhesion, and to minimise or prevent coverage of the stent 1 by ingrowth of intima. The flow pattern in the blood vessel including the swirling pattern induced by the non-planar geometry of the blood vessel operates to inhibit the development of vascular diseases such as thrombosis/atherosclerosis and intimal hyperplasia.

It will be appreciated that the shape of the stent may be varied.

Figure 9:
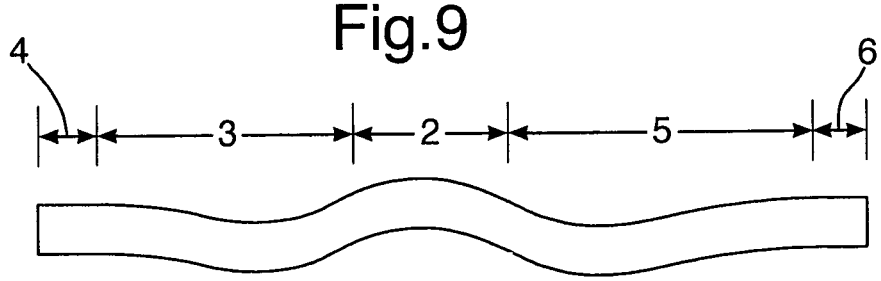
FIGS. 9 to 13 are side views of other stents according to the invention in the deployment configuration.

For example, as illustrated in FIG. 9, the central section 2 may be shorter in length than each of the intermediate sections 3, 5.

Figure 10:
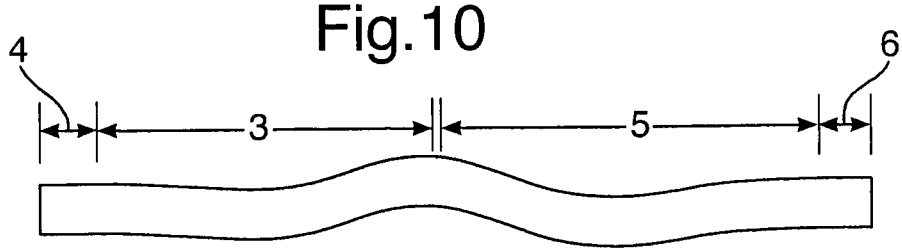

As illustrated in FIG. 10, the stent may comprise the first intermediate section 3, the first end section 4, the second intermediate section 5, and the second end section 6. In this case the stent does not include a central section.

Figure 11:
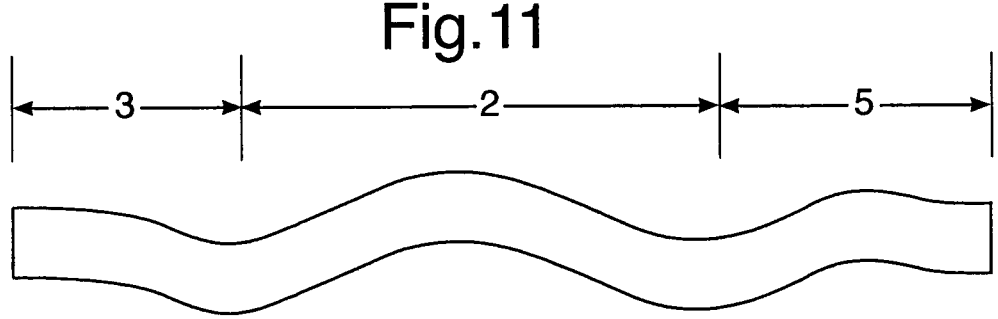

As illustrated in FIG. 11, the stent may comprise the central section 2, the first intermediate section 3, and the second intermediate section 5. In this case the stent does not include a first end section, or a second end section.

Figure 12:
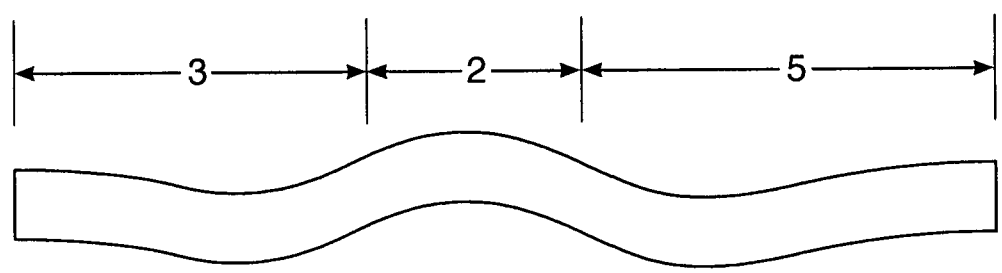

As illustrated in FIG. 12, the central section 2 may be shorter in length than each of the intermediate sections 3, 5.

Figure 13:
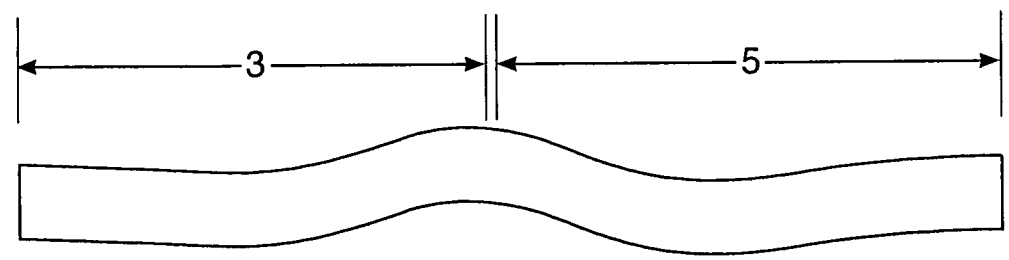

As illustrated in FIG. 13, the stent may comprise the first intermediate section 3, and the second intermediate section 5. In this case the stent does not include a central section, or a first end section, or a second end section.

Figure 14:
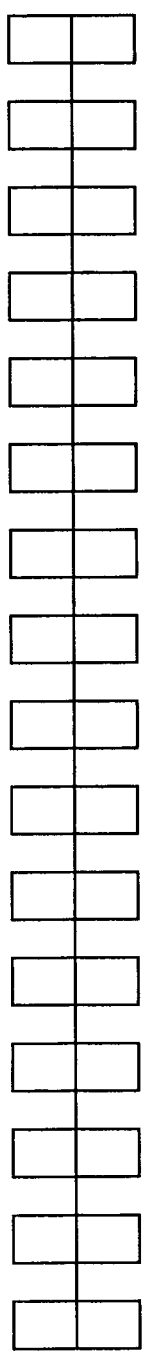
FIG. 14 is a side view of another stent according to the invention in the delivery configuration.
Figure 15:
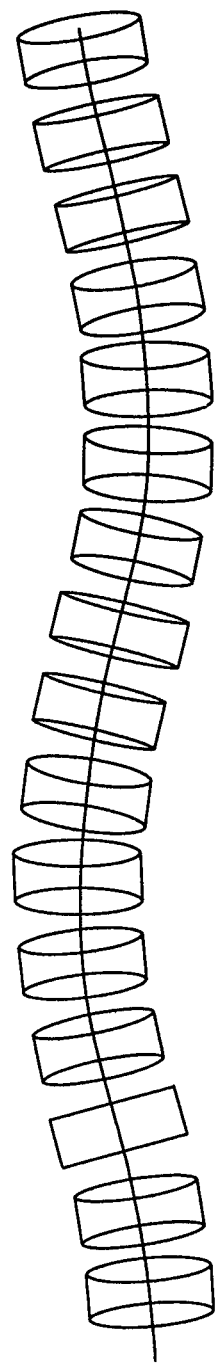
FIG. 15 is a side view of the stent of FIG. 14 in the deployment configuration.

It will be appreciated that in the deployment configuration the central section may have a piecewise helical shape, as illustrated in FIGS. 14 and 15. The stent may be formed of a series of annular elements in the form of short crown-shaped elements. Adjacent crowns are arranged in series and are linked by connector elements forming a tubular structure. Each crown is mostly cylindrical in shape having a straight centreline. The centreline of a straight stent is defined by a series of crown centrelines arranged in a co-linear fashion, as illustrated in FIG. 14. In certain embodiments of a three-dimensional stent, the crown centreline segments are no longer co-planar. In one such embodiment the stent centreline forms a piecewise linear three-dimensional curve. In another such embodiment the stent centreline is a series of discontinuous line segments, as illustrated in FIG. 15.

The central section may have an alternative shape, for example in the deployment configuration the central section may be substantially spiral shaped. Similarly the intermediate section may have an alternative shape, for example in the deployment configuration the intermediate section may be substantially spiral shaped.

Figure 16:
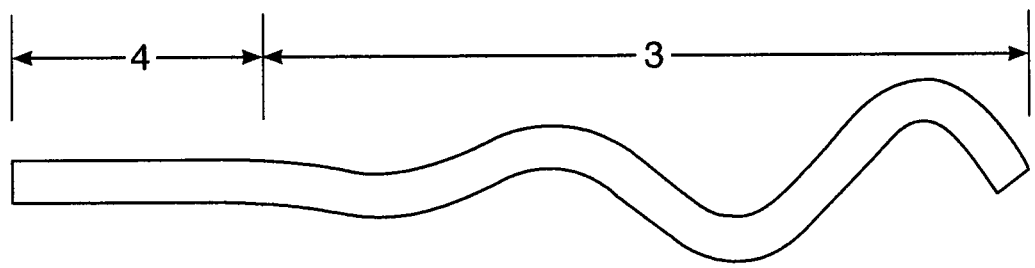
FIGS. 16 and 17 are side views of other stents according to the invention in the deployment configuration.

As illustrated in FIG. 16, the stent may comprise the first intermediate section 3, and the first end section 4. In this case the stent does not include a central section, or a second intermediate section, or a second end section. In the deployment configuration the first intermediate section 3 is substantially spiral shaped.

Figure 17:
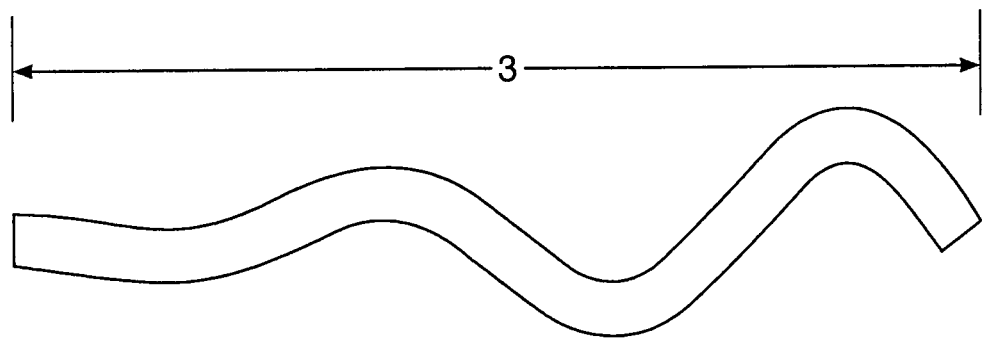

As illustrated in FIG. 17, the stent may comprise the first intermediate section 3 only. In this case the stent does not include a central section, or a first end section, or a second intermediate section, or a second end section. In the deployment configuration the first intermediate section 3 is substantially spiral shaped.

Figure 18:
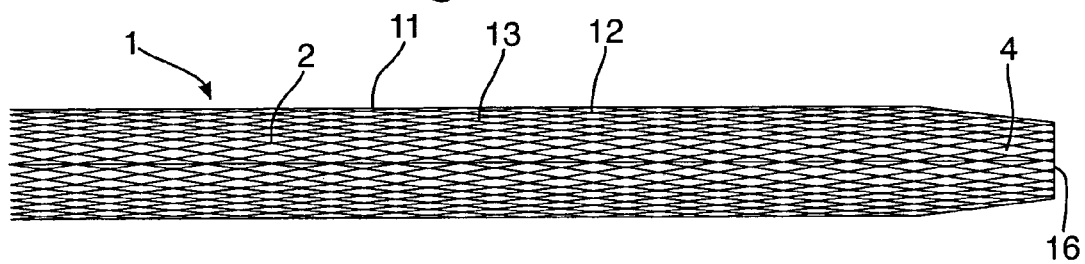
FIGS. 18, 19 and 20 are side views of parts of other stents according to the invention in the deployment configuration.
Figure 19:
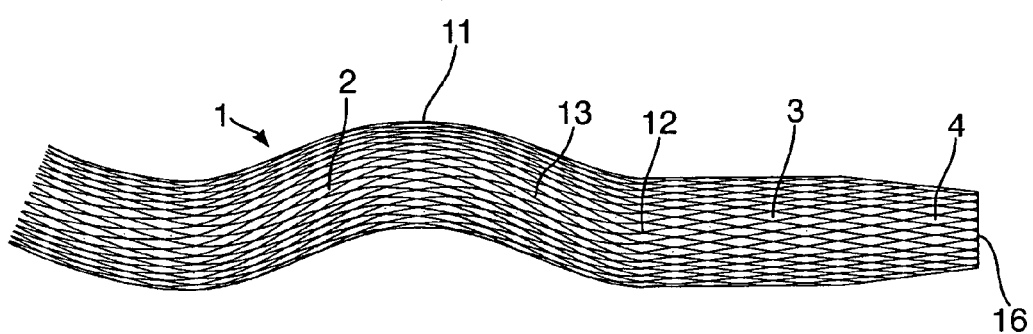
Figure 20:
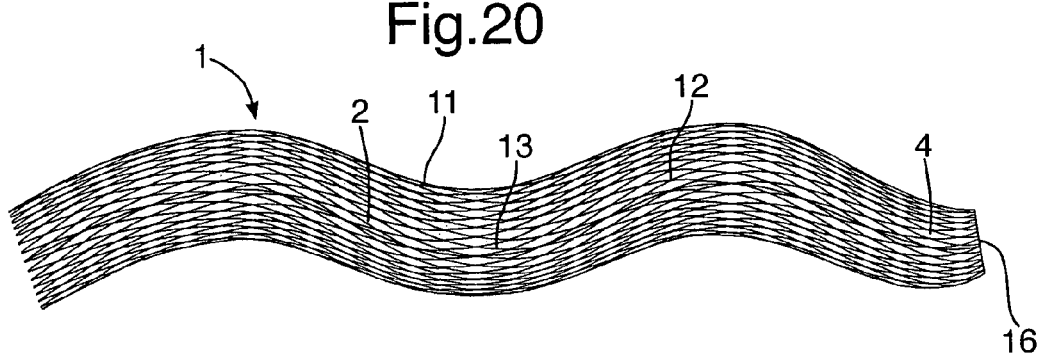

The embodiments of FIGS. 18, 19 and 20 are stents which when in the deployment configuration and not constrained in a blood vessel have a diameter which reduces towards the end of the stent.

The stent 1 shown in FIG. 18 has a cylindrical geometry when in the deployment configuration. The stent has a central section 2 and an end section 4. The diameter of the end section 4 reduces from the diameter of the central section 2 to a smaller diameter at the end 16 of the stent. The end section 4 is thus tapered or conical. The stent 1 is made up of annular elements 11, each annular element being formed of strut elements 13 in a zig-zag shape, and adjacent annular elements being connected by connecting elements 12.

The stent 1 of FIG. 19 has a central section 2, an intermediate section 3 and an end section 4. As in the case of the FIG. 18 stent, the stent is made up of annular elements 11 each formed of interconnected strut elements 13, with the annular elements 11 being connected by connecting elements 12. In this case, the central section 2 has a longitudinal axis which is curved in three-dimensional space, e.g. helical. This is connected to the intermediate section 3 which is of straight cylindrical form, and section 3 is in turn connected to end section 4 which is tapered, having a reducing diameter towards the end 16 of the stent.

In the case of the stent of FIG. 20, this has a central section 2 with a longitudinal axis curved in three-dimensional space, e.g. helical, which is connected to an end section 4 which is tapered. In this case, the end section 4, as well as being tapered, has a longitudinal axis which is curved in three-dimensional space.

When a stent according to FIG. 18 or FIG. 19 or FIG. 20 is deployed in a blood vessel, its diameter will be reduced along its length by the constraining action of the vessel. At the stent end 16, however, the diameter may not be reduced at all by the constraining action, or may be reduced only slightly, thereby avoiding a sharp change in the flow lumen of the stent between the unstented part and the stented part. Rather, a gradual change is provided over the length of the end section 4.

The other ends of the stents of FIG. 18 or 19 or 20 are not shown but may also have a taper and possibly the same construction as the ends which are shown.

The invention is not limited to the embodiments hereinbefore described, with reference to the accompanying drawings, which may be varied in construction and detail.

The invention claimed is:

1. A stent suitable for deployment in a blood vessel to support at least part of an internal wall of the blood vessel, the stent comprising a first end section at one longitudinal end thereof, a second end section at another longitudinal end thereof opposite to said one longitudinal end, and a section located between said first and second end sections, the stent extending longitudinally and having a centreline, the stent being movable between a delivery configuration and a deployment configuration, wherein:
   in the delivery configuration the centreline of the stent is straight; and
   in the deployment configuration the centreline of the stent in the section between the first and second end sections is curved in three-dimensional space, so that when the stent is in the blood vessel it causes at least a part of the longitudinal axis of the blood vessel to curve in three-dimensional space; and
   in the deployment configuration the centreline of the stent in the first end section thereof is straight, the centreline of the stent in the second end section thereof is straight, and the centreline of the stent in the first end section is co-linear with the centreline of the stent in the second end section.

2. A stent as claimed in claim 1 wherein in the deployment configuration, the three-dimensionally curved section is helically shaped, whereby the centreline is a helical line.

3. A stent as claimed in claim 1, wherein in the deployment configuration, the three-dimensionally curved section is spiral shaped.

4. A stent as claimed in claim 1, wherein in the delivery configuration, the three-dimensionally curved section is cylindrically shaped.

5. A stent as claimed in claim 1, wherein in the deployment configuration, the straight first and second end sections are cylindrically shaped.

6. A stent as claimed in claim 1, wherein the centreline of the three-dimensionally curved section is a helical line, the helical line having a helical angle, and wherein the helical angle varies along the length of the section.

7. A stent as claimed in claim 6, wherein the helical angle varies gradually along the length of the varying helical angle section.

8. A stent as claimed in claim 6, wherein the helical angle at one end of the varying helical angle section is in the range of from 5° to 60°.

9. A stent as claimed in claim 8, wherein the helical angle at one end of the varying helical angle section is in the range of from 15° to 45°.

10. A stent as claimed in claim 9, wherein the helical angle at one end of the varying helical angle section is approximately 30°.

11. A stent as claimed in claim 8, wherein the helical angle at the other end of the varying helical angle section is approximately 0°.

12. A stent as claimed in claim 1, wherein in the deployment configuration, the three-dimensionally curved section is helically shaped, whereby the centreline in that section is a helical line, the helical centreline being described by a radius of an imaginary cylinder on which it lies and the cylinder having a centreline.

* * * * *